(12) United States Patent
Katra et al.

(10) Patent No.: US 9,314,178 B2
(45) Date of Patent: Apr. 19, 2016

(54) CARDIAC SIGNAL RECORDING USING DYNAMICALLY GENERATED DETECTION THRESHOLDS

(71) Applicant: Greatbatch Ltd., Clarence, NY (US)

(72) Inventors: Rodolphe Katra, Blaine, MN (US); Niranjan Chakravarthy, Eden Prairie, MN (US)

(73) Assignee: GREATBACH, LTD., Clarence, NY (US)

( * ) Notice: Subject to any disclaimer, the term of this patent is extended or adjusted under 35 U.S.C. 154(b) by 54 days.

(21) Appl. No.: 14/209,035

(22) Filed: Mar. 13, 2014

(65) Prior Publication Data

US 2014/0276154 A1 Sep. 18, 2014

Related U.S. Application Data

(60) Provisional application No. 61/785,642, filed on Mar. 14, 2013.

(51) Int. Cl.
*A61B 5/04* (2006.01)
*A61B 5/042* (2006.01)
*A61B 5/0464* (2006.01)
*A61B 5/024* (2006.01)
*A61B 5/046* (2006.01)

(52) U.S. Cl.
CPC ............ *A61B 5/04012* (2013.01); *A61B 5/0422* (2013.01); *A61B 5/0464* (2013.01); *A61B 5/024* (2013.01); *A61B 5/046* (2013.01)

(58) Field of Classification Search
CPC ...................... A61B 18/1206; A61B 2019/461; A61B 2019/566; A61B 19/56; A61B 2019/564; A61B 19/50; A61B 2018/00761; A61B 2018/00702; A61B 2018/0075; A61B 18/1492; A61B 2018/00839
See application file for complete search history.

(56) References Cited

U.S. PATENT DOCUMENTS

| 7,421,292 | B1 * | 9/2008 | Kroll ............................. 600/518 |
| 7,769,436 | B1 | 8/2010 | Boileau et al. |
| 2009/0156908 | A1 | 6/2009 | Belalcazar et al. |

FOREIGN PATENT DOCUMENTS

WO WO2012057860 5/2012

OTHER PUBLICATIONS

EP Search Report from EP Application No. 14159848.2 dated Jun. 24, 2014, 7 pages.

* cited by examiner

*Primary Examiner* — Rex R Holmes
(74) *Attorney, Agent, or Firm* — Hollingsworth Davis, LLC

(57) ABSTRACT

A medical device includes a housing configured for implantation within a body of a patient, and detection circuitry disposed in the housing and coupled to an electrode arrangement. The detection circuitry is configured to sense cardiac signals from the patient. A processor is coupled to the detection circuitry. The processor is configured to compare the cardiac signals to an initial detection threshold, automatically generate an additional detection threshold in response to a predetermined number of the cardiac signals meeting or exceeding the initial detection threshold or a previously generated detection threshold, count each occurrence of a cardiac signal meeting or exceeding each of the respective detection thresholds, and record cardiac signal data only for a cardiac signal that meets or exceeds the highest of the detection thresholds.

20 Claims, 13 Drawing Sheets

CARDIAC SIGNAL RECORDING USING DYNAMICALLY GENERATED DETECTION THRESHOLDS

RELATED APPLICATIONS

This application claims the benefit of Provisional Patent Application Ser. No. 61/785,642, filed on Mar. 14, 2013, to which Applicant claims priority under 35 U.S.C. §119(e), and which is incorporated herein by reference in its entirety.

TECHNICAL FIELD

This patent document pertains generally to cardiac signal monitoring and more particularly, but not by way of limitation, to systems and methods that provide for efficient recording of cardiac signals using dynamically generated detection thresholds.

BACKGROUND

Electrical signals cause a heart to beat. In a healthy patient, regular heart beats pump blood through the cardiovascular system. The human cardiovascular system is responsible for receiving oxygen-deprived blood into the heart from the venous system of the body, delivering the oxygen-deprived blood to the lungs to be replenished with oxygen, receiving the oxygenated blood from the lungs back into the heart, and delivering the oxygenated blood to the body via the arterial vasculature. This process is regulated within the heart by electrical pulses that control operation of the heart's receiving and pumping chambers.

In a healthy heart, the sinoatrial node of the heart generates electrical pulses in a consistent and regulated fashion to regulate receiving and pumping blood in the heart's chambers. The electrical impulses propagate as activation wavefronts across the atria, the upper chambers of the heart, and cause cells of the atria to depolarize and contract, which forces blood from the atria to the ventricles, the lower chambers of the heart. The ventricles receive the blood from the atria, and the wavefront, after passing through the atrioventricular node and moving to the Purkinje system, moves to cells of the ventricles causing the ventricles to contract and pump the blood to the lungs and to the rest of the body.

Various aspects of cardiac activity (e.g., heart rate, arrhythmias) can be detected by measuring, recording, and analyzing cardiac electrical signals, such as an electrocardiogram (ECG) signal. One way of measuring ECG signals involves attaching electrodes, typically ten, externally to a patient's skin and sensing the electrical signals that form the ECG waveform. Implantable monitoring systems can be implanted under the skin with electrodes that sense subcutaneous electrical signals, including ECG signals, which are analyzed as being indicative of cardiac activity.

SUMMARY

Embodiments of the disclosure are directed to methods and devices that implement an automatic detection threshold adaptation scheme for assessing patient status. According to some embodiments, a method involves sensing cardiac signals and comparing the signals to an initial detection threshold. The method also involves automatically generating an additional detection threshold in response to a predetermined number of the cardiac signals meeting or exceeding the initial detection threshold or a previously generated detection threshold. For each of the detection thresholds, the method involves counting each occurrence of a cardiac signal meeting or exceeding each detection threshold. The method further involves recording cardiac signal data only for a cardiac signal that meets or exceeds the highest of the detection thresholds.

In accordance with other embodiments, a method involves (a) setting an initial detection threshold $Th_1$ and an occurrence threshold X, where X is a positive integer, and (b) sensing cardiac signals from a patient. The method also involves (c) recording cardiac signals up to X times in response to sensing cardiac signals that meet or exceed the initial detection threshold $Th_1$, and (d) automatically generating an additional detection threshold $Th_2$ in response to sensing X cardiac signals that meet or exceed the initial detection threshold $Th_1$. The method further involves, (e) in response to sensing up to Y cardiac signals that meet or exceed the additional detection threshold $Th_2$, (i) recording cardiac signals that meet or exceed the additional detection threshold $Th_2$ up to Y times, and (ii) automatically generating another additional detection threshold $Th_3$. The method also involves, (f) for each of the respective detection thresholds $Th_1$, $Th_2$, and $Th_3$, counting each occurrence of a cardiac signal that meets or exceeds each respective detection threshold, $Th_1$, $Th_2$, and $Th_3$. The method may further involve repeating processes (d) and (e) a number of times in response to sensing a predetermined number of cardiac signals that meet or exceed a previously generated detection threshold.

According to further embodiments, a medical device includes a housing configured for implantation within a body of a patient, and detection circuitry disposed in the housing and coupled to an electrode arrangement. The detection circuitry is configured to sense cardiac signals from the patient. A processor is coupled to the detection circuitry. The processor is configured to compare the cardiac signals to an initial detection threshold, automatically generate an additional detection threshold in response to a predetermined number of the cardiac signals meeting or exceeding the initial detection threshold or a previously generated detection threshold, count each occurrence of a cardiac signal meeting or exceeding each of the respective detection thresholds, and record cardiac signal data only for a cardiac signal that meets or exceeds the highest of the detection thresholds.

The above summary is not intended to describe each disclosed embodiment or every implementation of the present disclosure. The figures and the detailed description below more particularly exemplify illustrative embodiments

BRIEF DESCRIPTION OF THE DRAWINGS

Throughout the specification reference is made to the appended drawings, where like reference numerals designate like elements, and wherein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
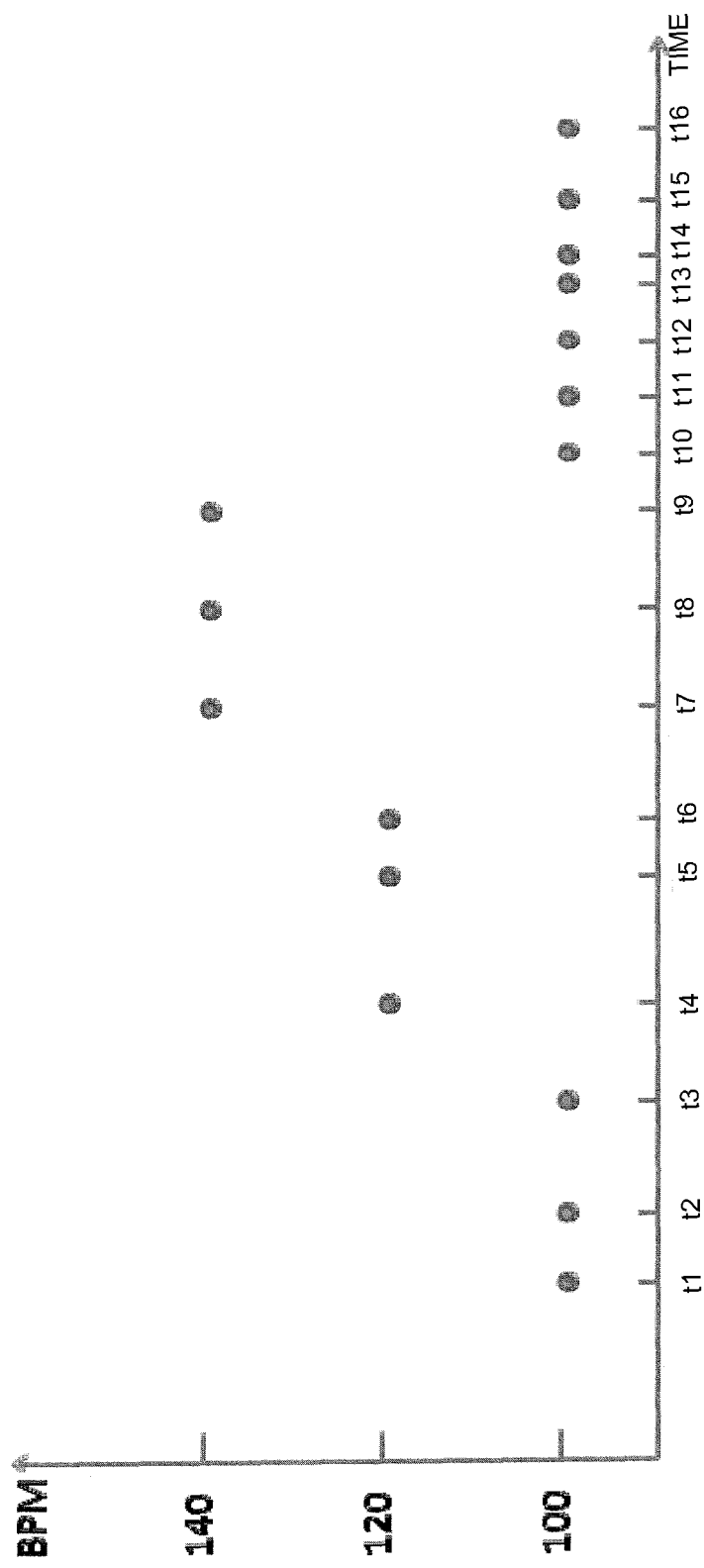
FIG. 1 illustrates an adjustable detection threshold methodology that can be implemented by a patient monitoring device in accordance with various embodiments.

Cardiac monitoring devices, such as implantable loop records (ILRs), can be implemented to monitor and detect various types of ECG events (e.g., tachycardia, bradycardia, asystole, atrial fibrillation, ventricular fibrillation) based on preset parameters, such as detection thresholds. Detection thresholds, for example, can be programmed by a physician and downloaded to an ILR via a patient-external personal diagnostic monitor (PDM), which is configured to wirelessly communicate with the ILR. Using conventional approaches, all subsequent cardiac event captures occur based on the preset parameters. The present inventors have recognized, among other things, that if the parameters are improperly set, it can lead to excessive cardiac event captures and transmissions leading to reduction and/or loss of battery and memory resources, as well as generating excessive amounts of data that may not be diagnostically relevant. For example, if a tachycardia threshold is improperly set at 80 beats per minute (bpm), a normal patient can frequently exceed this limit, leading to excessive asymptomatic ECG recording (e.g., ECG strip capture). Hence, there is an unmet need to increase device longevity and detection accuracy while preserving diagnostically relevant information and physician recommendations.

In the following detailed description, the examples are described in sufficient detail to enable those skilled in the art to practice the invention, and it is to be understood that other examples may be utilized and that structural changes may be made without departing from the scope of the present invention. Therefore, the following detailed description is not to be taken in a limiting sense.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, or process that includes elements in addition to those listed after such a term are still deemed to fall within the scope of the description. Moreover, the terms "first," "second," and "third," etc. are used merely as labels, and are not intended to impose numerical requirements on their objects.

For purposes of explanation, and not of limitation, the following description considers tachycardia episodes as cardiac events of interest. It is understood that the features and concepts disclosed herein can readily be extended to other rhythm and episode types, such as bradycardia, asystole, atrial fibrillation, and ventricular fibrillation, among others.

Various embodiments are directed to cardiac signal recording devices and methods using dynamically generated detection thresholds. Particular embodiments are directed to closed-loop implementations, in which cardiac event detection thresholds are automatically adjusted in response to events detected during cardiac rhythm monitoring. In accordance with a typical "open-loop" mode of cardiac rhythm monitoring, a physician sets a tachycardia threshold on some type of programming device (e.g., a PDM), which is then transferred to the ILR for tachycardia event capture. Whenever a detected ECG heart rate exceeds this set threshold, an asymptomatic event capture occurs, and the captured strip is transmitted to the PDM. In a "closed-loop" mode of cardiac rhythm monitoring, by contrast, the physician sets a preferred (e.g., initial) tachycardia threshold on the PDM which is transferred to the ILR during the start of monitoring. Depending on the events detected during cardiac rhythm monitoring, the detection threshold scheme is adjusted automatically, such as by the generation of additional detection thresholds and, optionally, removal of one or more of the additional detection thresholds.

Automatic adjustment of cardiac event detection thresholds can be based on a variety of objectives, such as a desired savings of memory resources, battery (power) resources, or a combination of these or other resources/objective, for example. Factors that can drive or influence automatic adjustment of cardiac event detection thresholds can include one or more of reducing collection data burden, tracking disease progression, input by other sensors (e.g., modulating detection thresholds in response to one or more sensor signals), and adaptive tracking of patient function or lifestyle. The number and increments between the detection thresholds may be based on one or more of a fixed percentage, patient demographics and characteristics (e.g., gender, disease type, age), physician preset increments, other markers derived from the ECG, a histogram, standard deviation from a mean value, increments have varying resolution (e.g., increment size) either increasing or decreasing, and an adaptive assessment, such as one that is reconciled with physician non-parametric input. Other factors and considerations are contemplated beyond those listed for illustrative purposes.

According to various embodiments, when a patient's detected ECG heart rate exceeds an initial (e.g., physician preset) detection threshold, $Th_1$, these events are captured by the patient monitoring device (e.g., ILR). Such an event capture occurs X times, where X is a positive integer set by the physician or preset in the system. Once X strips have been captured by the device within a defined time period, the device or PDM communicatively coupled thereto automatically increases the detection threshold. For example, the detection threshold can be adjusted according to the formula: [new threshold=old threshold, $Th_1$+Delta] or [new threshold, $Th_2$=old threshold, $Th_1$*Delta].

A detection threshold adaptation scheme according to various embodiments uses various time limits when generating and removing detection thresholds and during other operations. For example, a time limit can be established for sensing for X cardiac events that exceed an initial detection threshold, $Th_1$, and the same or different time limit for sensing for Y cardiac events that exceed an additional detection threshold, $Th_2$. The time limits can be preset by the physician or developed by the device in a closed-loop manner during patient monitoring. Time limits can be set or established in terms of hours or days, for example. Detection time limits for increasing cardiac activity (e.g., adding additional detection thresholds) can be the same or different from those for decreasing cardiac activity (e.g., removing or reducing detection thresholds). Time periods can differ based on different patient and device conditions/factors (e.g., bradycardia vs. tachycardia condition, patient-specific condition such as disease condition, increasing or decreasing the detection threshold, and a detection reaching a boundary condition, such as a minimum or maximum condition).

The detection threshold adaptation scheme can be additive or multiplicative, and can be patient-specific or based on other studies and population metrics, for example. The adaptation Delta (Delta increment) can also be patient-specific or based on population metrics. After such a threshold revision and, depending on system configuration, communication from the PDM to the ILR, the following processes can be implemented according to various embodiments: (a) the ILR captures ECG strips only when the heart rate exceeds the new adapted threshold, and (b) the ILR raises a flag or counts the occurrence (but does not capture or store an episode strip) when the heart rate exceeds the older (including physician-set) thresholds. Step (a) ensures 'interesting' increases in tachycardia levels are captured but excessive rhythm captures based on lower thresholds do not occur, and step (b) ensures that the prescribing physician gets the diagnostic information set during device implant, namely, strips corresponding to start-up tachycardia limits and instances when the threshold is increased.

The above processes are iterated with the adaptive threshold being revised up or down in a feedback mechanism; with hard limits on the upper and lower bounds in various implementations. According to various embodiments, a closed-loop automatic detection threshold adjustment methodology can be patient-specific, yields additional diagnostic information (e.g., changing tachycardia threshold limits over time which could be correlated to medication, or changes to the disease condition) and provides for optimized rhythm captures, resulting in longer battery life and efficient memory utilization.

The following is a representative example of a closed-loop method for tachycardia event capture using a dynamic detection threshold adaptation scheme in accordance with various embodiments. It is understood that a detection threshold adaptation scheme according to the present disclosure can be implemented for a variety of cardiac and other patient conditions. For example, automatic detection threshold adaptation can be implemented for bradycardia thresholds, ventricular arrhythmia thresholds, and atrial arrhythmia thresholds, for example.

With reference to FIG. 1, the following representative example shows how a closed-loop detection threshold adaptation scheme can capture all exemplary tachycardia events, ensure that physician-required preset threshold-based diagnostic information is available, track a patient's "tachycardia level state," and optimize data capture and transmission. It is assumed in this representative example that a physician sets the tachycardia detection threshold at 100 bpm, the threshold increment (Delta) is +/−20 bpm, and the number of strip captures X=2. It is further assumed that the patient's tachycardia state varies over time as follows (i.e., the patient experiences tachycardia at these different heart-rate levels over time). For this representative example closed-loop method, the event captures/flags are as follows:

| Time | BPM vs Tachycardia Threshold | Capture/Flag | Counts and Thresholds |
|---|---|---|---|
| t1 | BPM ≥ New Threshold (100) | 100 bpm capture | 100 bpm capture count = 1 |
| t2 | BPM ≥ New Threshold (100) | 100 bpm capture | 100 bpm capture count = 2<br>New Threshold = 100 + 20 = 120 |
| t3 | BPM ≥ Old Threshold (100)<br>BPM < New Threshold (120) | 100 bpm flag<br>No 120 bpm capture | 100 bpm flag count = 1<br>120 bpm capture count = 0 |
| t4 | BPM ≥ Old Threshold (100)<br>BPM ≥ New Threshold (120) | 100 bpm flag<br>120 bpm capture | 100 bpm flag count = 2<br>120 bpm capture count = 1 |
| t5 | BPM ≥ Old Threshold (100)<br>BPM ≥ New Threshold (120) | 100 bpm flag<br>120 bpm capture | 100 bpm flag count = 3<br>120 bpm capture count = 2<br>New Threshold = 120 + 20 = 140 |
| t6 | BPM ≥ Old Threshold (100)<br>BPM ≥ Old Threshold (120)<br>BPM < New Threshold (140) | 100 bpm flag<br>120 bpm flag<br>No 140 bpm capture | 100 bpm flag count = 4<br>120 bpm flag count = 1<br>140 bpm capture count = 0 |

-continued

| Time | BPM vs Tachycardia Threshold | Capture/Flag | Counts and Thresholds |
|---|---|---|---|
| t7 | . | 100 bpm flag | 100 bpm flag count = 5 |
|  | . | 120 bpm flag | 120 bpm flag count = 2 |
|  | . | 140 bpm capture | 140 bpm capture count = 1 |
| t8 | . | 100 bpm flag | 100 bpm flag count = 6 |
|  | . | 120 bpm flag | 120 bpm flag count = 3 |
|  | . | 140 bpm capture | 140 bpm capture count = 2 |
|  |  |  | New Threshold = 140 + 20 = 160 |
| t9 | . | 100 bpm flag | 100 bpm flag count = 7 |
|  | . | 120 bpm flag | 120 bpm flag count = 4 |
|  | . | 140 bpm flag | 140 bpm flag count = 1 |
|  | . | No 160 bpm capture | 160 bpm capture count = 0 |
| t10 | . | 100 bpm flag | 100 bpm flag count = 8 |
|  |  |  | 120 bpm flag 120 count = 4 (no increase) |
|  |  |  | 140 bpm flag count = 1(no increase) |
|  |  |  | Since no increase over a predetermined time period, New Threshold = 160 − 20 = 140 |
| t11 | . | 100 bpm flag | 100 bpm flag count = 9 |
|  | . |  | 120 bpm flag count = 4 (no increase) |
|  | . |  | 140 bpm flag count = 1 (no increase) |
|  |  |  | Since no increase over a predetermined time period, New Threshold = 140 − 20 = 120 |
| t12 | . | 100 bpm flag | 100 bpm flag count = 10 |
|  | . |  | 120 bpm flag count = 4 (no increase) |
|  | . |  | 140 bpm flag count = 1(no increase) |
|  |  |  | Since no increase over a predetermined time period, New Threshold = 120 − 20 = 100 |
| t13 | . | 100 bpm capture | 100 bpm capture count = 1 (after reset) |
| t14 | . | 100 bpm capture | 100 bpm capture count = 2 |
|  |  |  | New Threshold = 100 + 20 = 120 |
| t15 | . | 100 bpm flag | 100 bpm flag count = 11 |
|  | . | No 120 bpm capture |  |
| t16 | . | 100 bpm flag | 100 bpm flag count = 12 |

In this illustrative closed-loop adaptive detection threshold method, there were 8 ECG captures and 12 event flags (e.g., 100, 120, 140 bpm flags). Notably, all exemplary tachycardia events at different rates were captured and physician-required diagnostic information on the number of 100 bpm threshold information is also available. Further, it can be seen that the changes in adaptive detection threshold level tracks patient "tachycardia level state." Finally, with respect to the data capture and transmission, if each event capture involved capturing and saving a 60 second ECG strip sampled at 200 samples per second, the number of data points captured with the closed-loop adaptive method would equal 8*60*200+ 12=96,012 data points. By way of comparison, using an open-loop scheme where all events≥preset 100 bpm threshold are captured, the number of data points would be 16*60*200=198,000 data points. In this illustrative example, a 50% savings (e.g., in memory) can be achieved with the above adaptive method parameters.

It is noted that the level of event capture optimization will depend on the adaptation parameters (e.g., if X is very large, there could be insignificant savings with the closed-loop method). X, the number of event captures, can be patient-specific, patient state-specific (e.g., post ablation X may be set to a higher value) or population-based, for example. In some embodiments where a number of ECG strips are recorded (e.g., X is a larger number), it may be desirable for the device two select between ECG strips captured for the same bin or zone for preservation and/or transmission to a PDM or other patient-external device. Selecting between ECG strips captured for the same bin or zone (e.g., the bpm range between adjacent detection thresholds) can allow less useful strips to be discarded, thereby freeing up valuable memory resources. ECG strip selection can be based on one or more factors, such as the ECG strip with highest specificity and sensitivity, the strip with the cleanest data (e.g., highest signal-to-noise ratio), and the ECG strip corresponding to a particular time of day, for example.

According to some implementations, a closed-loop adjustable detection threshold scheme can be adaptive based on the event capture sensitivity and specificity (i.e., accuracy). For example, if the sensitivity is high and the specificity is low, the detection threshold can be increased. If the sensitivity is high and the specificity is high, the detection threshold can be kept the same. If the sensitivity is low and specificity is high, the detection threshold can be decreased. The assessment of sensitivity and specificity can be implemented in isolation or in combination with other embodiments of threshold adaptation.

Some embodiments can be implemented to address situations when the tachycardia limits are set too high for detection, such as due to inadequate patient history or operator error. In such embodiments, the device can down-regulate the detection threshold in case there is no event detection over a certain time period (e.g., 3 days) or if the maximum achieved patient heart rate is less than a certain percentage of the preset threshold (e.g., maximum heart rate over a day's duration is only 60% of the preset threshold). The updated (adapted) tachycardia detection threshold can be used as a benchmark for subsequent detections and event totals.

In some embodiments, other optimization cost functions can be used. In other embodiments, a closed-loop adaptive detection threshold method can be extended to trending ECG captures to change the capture frequency. As previously mentioned, a closed-loop adaptive detection threshold methodology can be extended to other types of cardiac events, such as threshold of R-R variability and/or a derivative thereof, and/or the detected presence of a P-wave or R-wave, and is not limited to tachycardia detection. A closed-loop adaptive detection threshold method can be automated or manual (e.g., based on clinician/IDTF monitoring or interrogation).

Although described herein with reference to an ILR, the presently-described examples can be used in other implanted measurement systems (e.g., ICD/CRT, pacemakers) or other surface (patient-external) measurement systems, where conserving power and memory is important. These and other similar devices are collectively referred to herein as a patient monitoring device, understanding that such a device may include a therapy delivery capability according to various embodiments.

Figure 2:
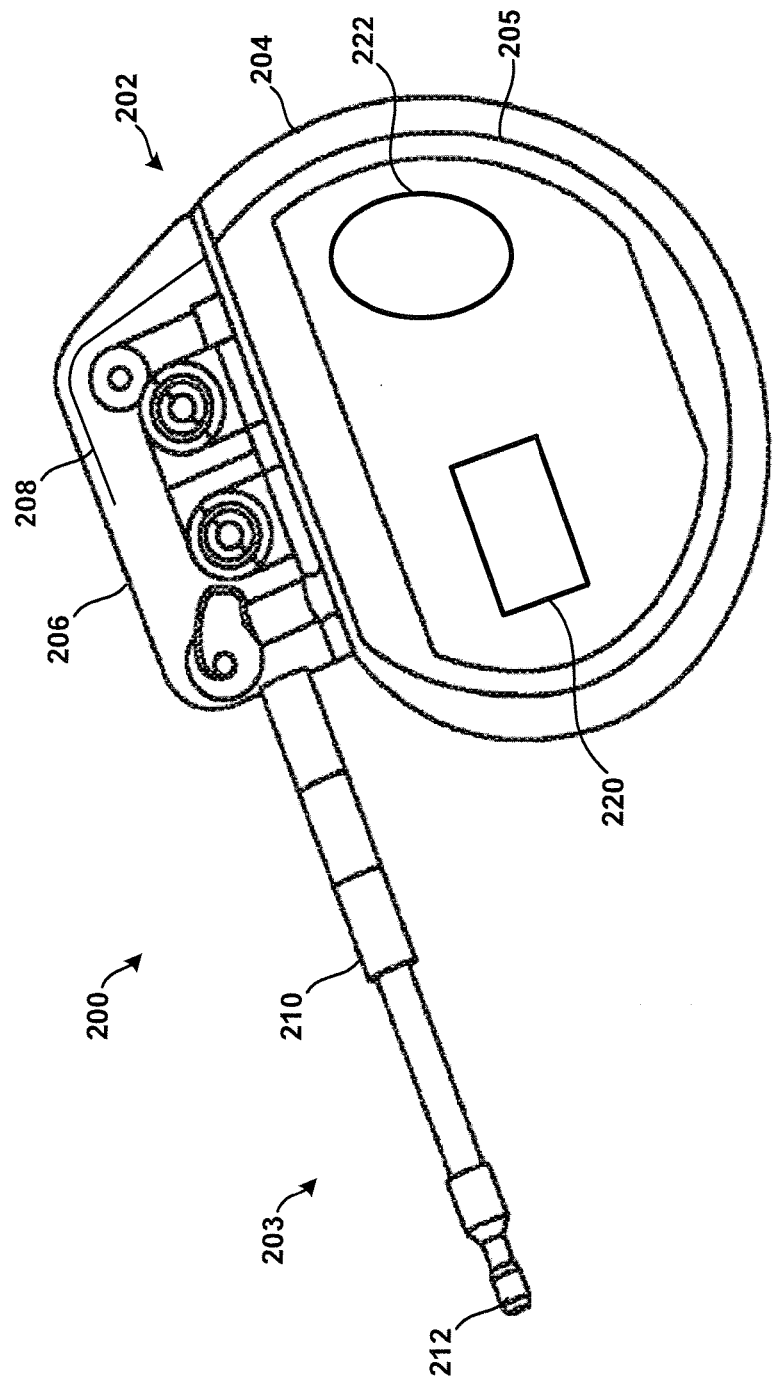
FIG. 2 illustrates a representative implantable device that can be subcutaneously implanted under a patient's skin, typically in a pectoral region of a patient's thorax, in accordance with various embodiments.
Figure 3:
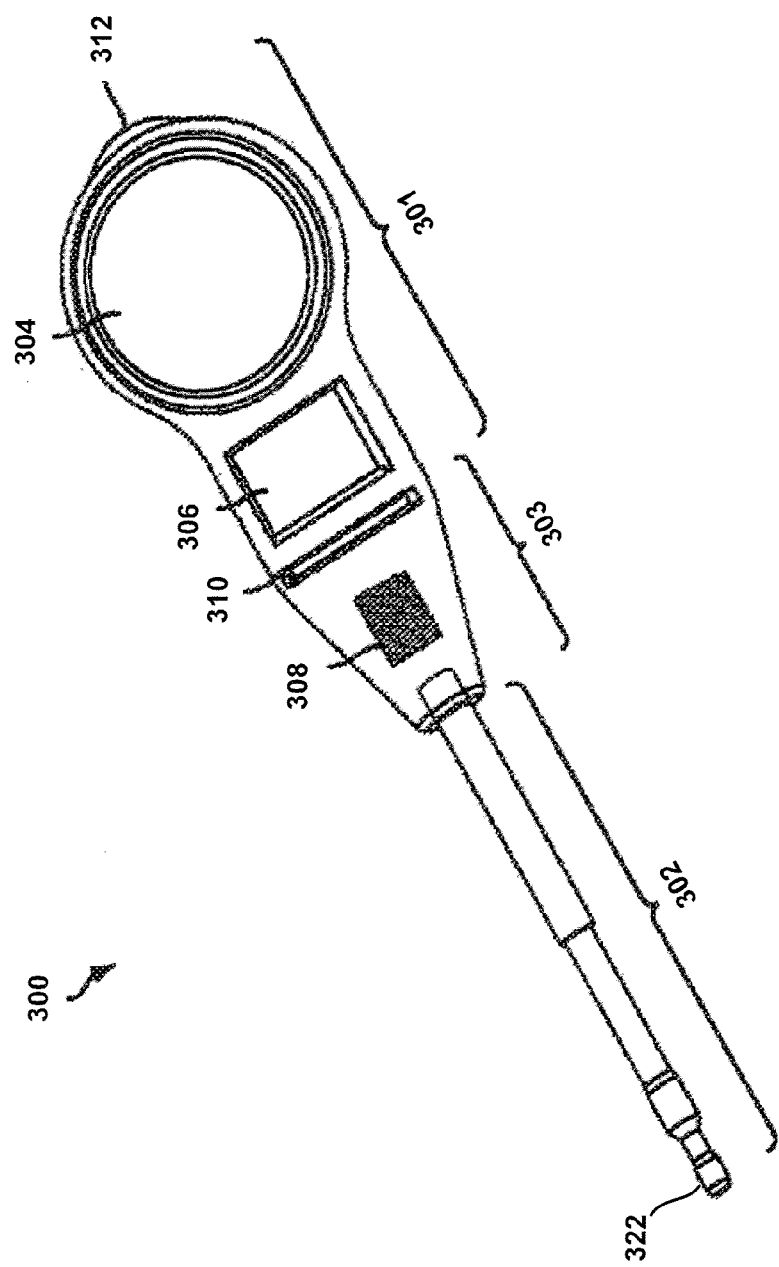
FIG. 3 illustrates a representative implantable device that can be subcutaneously implanted under a patient's skin in accordance with other embodiments.

In accordance with various embodiments, a patient monitoring device may be implemented as an implantable loop recorder, which may be leadless or may include one or more subcutaneous leads. Two representative embodiments of such a patient monitoring device are illustrated in FIGS. 2 and 3. Each of the patient monitoring devices illustrated in FIGS. 2 and 3 is configured to record an electrical physiologic signal, such as an EGG signal for the patient, from which various diagnostic information can be derived. It is understood that the devices illustrated herein are disclosed for illustrative purposes, and that methods and apparatuses of the present disclosure may be implemented in a variety of implantable and external embodiments.

FIG. 2 illustrates a representative patient monitoring device 200 that can be subcutaneously implanted under a patient's skin, typically in a pectoral region of a patient's thorax, in accordance with various embodiments. The device 200 may be a minimally invasive implantable monitoring device that senses and records a physiologic parameter, such as electrical activity of the heart, within a body of a patient. In some implementations, the device 200 is an implantable monitoring device that senses and records a physiologic parameter, such as an ECG signal, within the body of the patient and wirelessly transmits information associated with the physiologic parameter to an external device or system. Such a monitoring-only device that records cardiac electrical information may be implanted in a human patient for a relatively short period of time, such as a few months for example.

Other physiologic parameters or combinations of parameters, such as other electrical physiologic signals (e.g., EMG signal, bio-impedance signal), mechanical signals (e.g., blood pressure signal, blood flow signal, pulse oximetry), chemical signals (e.g., glucose), temperature and the like may similarly be recorded by the device 200 in various implementations. A dynamic detection threshold methodology according to the present disclosure can be implemented for a device comprising one or a multiplicity of physiologic sensors, each having its specific detection threshold optimization scheme. The description that follows will focus without limitation on implementations where the device 200 is used to monitor a subcutaneous ECG signal, but in other implementations such monitoring could be combined with or substituted by other monitoring functions.

The implantable device 200 shown in FIG. 2 includes a proximal section 202 and a distal section 203. The proximal section 202 includes a housing 204 within which various components of the device 200 are disposed, including electronic circuitry 220 and a battery 205, which may be single-use or rechargeable in various implementations. The housing 204 may be configured to include one or more electrodes, an example of which is shown as electrode 222. All or a portion of the housing 204 may be configured as an "active can," and may further include an indifferent electrode (not shown) which is electrically isolated from the housing electrode(s) 222. A header 206 is connected to the housing 204 and to a distal extension 210, which is generally flexible or shapeable. A distal electrode 212 is disposed at a distal end of the extension 210. The header 206 serves to electrically couple the distal electrode 212 and any other electrical or optical component of the distal extension 210 with components within the housing 204 (e.g., electronic circuitry 220). An antenna 208 is shown extending from the housing 204 and into the header 208. The antenna 208 is configured for telemetering data from the implantable device 200, and can be configured to effect bi-directional wireless communication with a patient-external device or system. In some embodiments, the antenna 208 can be incorporated into the distal extension 210.

FIG. 3 illustrates a representative patient monitoring device 300 that can be subcutaneously implanted under a patient's skin, typically in a pectoral region of a patient's thorax, in accordance with other embodiments. The representative device 300 generally includes three sections: a proximal section 301, a distal extension 302, and a midsection 303 between the proximal section 301 and the distal extension 302. The proximal section 301 is configured to hermetically house a battery 304, which may be single-use or rechargeable in various implementations, and electronic circuitry 306 (e.g., an electronics module) for performing actions consistent with the device's intended purpose. Without limitation, examples of actions that may be performed with some implementations of the device 300 include measuring one or more physiologic signals, storing the measured signal(s) in memory within the device 300, processing collected data, and wirelessly transmitting or receiving information to/from an external device, among others.

The midsection 303 may include a non-hermetic external surface, and may be designed to enclose or embed components suited for housing in a non-conductive enclosure, such as components that communicate by field or wave properties that may otherwise be impeded by a conductive housing. In this implementation, the midsection 303 houses an antenna 308 for wirelessly transmitting data to an external device or wirelessly receiving data from an external device. In some implementations, the midsection 303 can include a charging coil (not shown) that can be excited (e.g., with an external charging coil placed in proximity to the implant location) to recharge a rechargeable battery 304 of the device 300. Hermetic feedthroughs 310 may be provided where electrical connections enter or exit the hermetic proximal section 301 from the non-hermetic midsection 303 to maintain hermeticity of the proximal section 301.

The distal extension 302 may be a flexible subcutaneous lead attached to the midsection 303 at one end. Lead 302 may include one or more electrodes, such as distal electrode 322, for measuring electrical activity or stimulating body tissue. In some implementations, the distal extension 302 can serve as the telemetry antenna for the device 300, and in these cases the depicted antenna 308 may be omitted. In some implementations, the telemetry antenna function is incorporated into the distal extension (lead) 302 independent from any ECG sensing lead functionality. The device 300 may include a feature on an exterior surface to facilitate grasping of the device 300 during extraction. For example, a retraction loop 312 near the proximal end 301 of the device 300 may be grasped or hooked in this fashion for ease of retraction. The loop 312 may in addition, or in the alternative, be configured as a suture hole to facilitate anchoring of the device 300 via a suture.

The devices 200 and 300 shown in FIGS. 2 and 3 may include one or more electrodes for electrically interfacing to surrounding tissue for the purpose of sensing electrical activity. In some implementations, devices 200 and 300 include two electrodes, such as a proximal electrode and a distal electrode, and may measure a potential difference (e.g., a subcutaneous ECG signal) between the proximal and distal electrodes. The electrodes may be located on the devices 200 and 300 to increase (e.g., maximize) signal vector length of a measured physiologic signal. In general, measured amplitude of a sensed physiologic signal, such as an ECG signal, will vary with device placement and orientation within the patient. Sensed signal amplitude may also be related to separation distance between the measuring electrodes. Positioning the proximal and distal electrodes near opposing ends (e.g., near opposite longitudinal ends) of the devices 200 and 300 can increase (e.g., maximize) the amplitude of the sensed physiologic signal for a given device length, which may lead to better measurement results. In other implementations, the devices 200 and 300 can include three electrodes, though any suitable number (one, two, three, four, five, etc.) may be used in other implementations. In some implementations, one or more of the electrodes of the devices 200 and 300 may comprise excitation electrodes or combination excitation/sense electrodes. By way of example, the devices 200 and 300 may measure a bio-impedance for diagnostic purposes by injecting a known current between two electrodes and measuring a resulting voltage between two electrodes.

Figure 4:
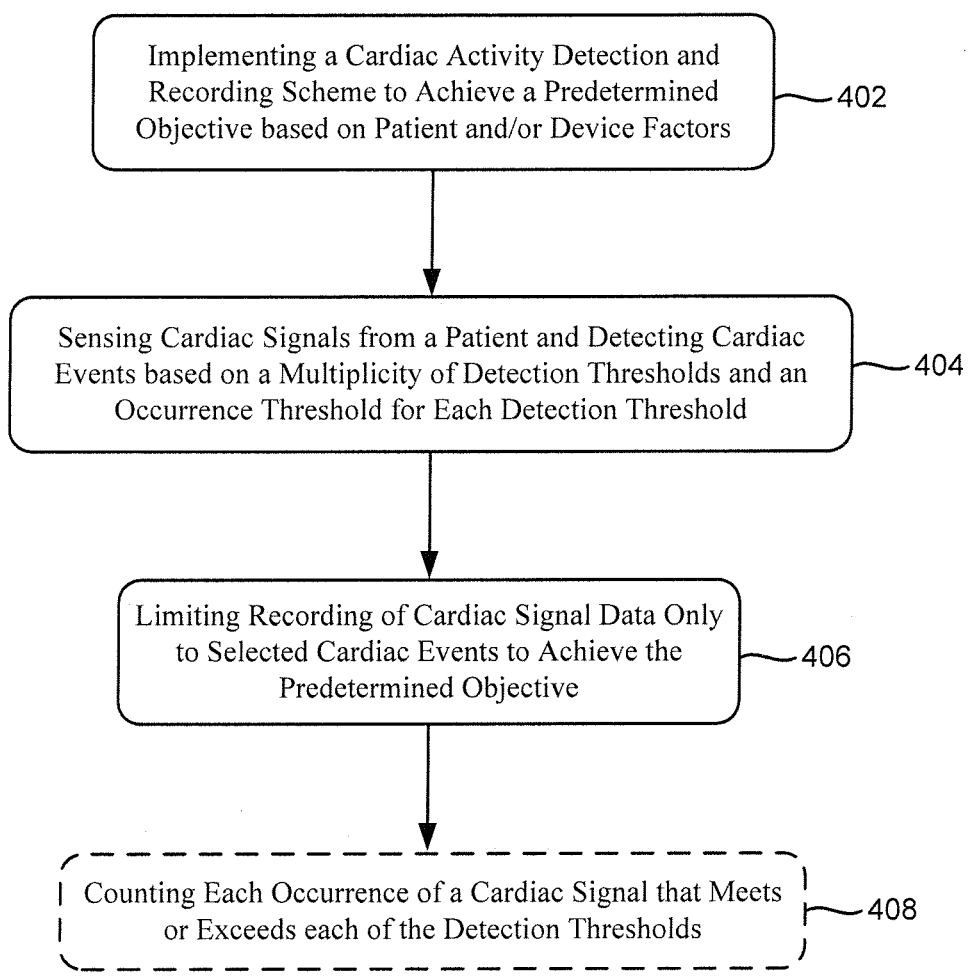
FIG. 4 illustrates an adjustable detection threshold methodology that can be implemented by a patient monitoring device in accordance with other embodiments.

Turning now to FIG. 4, there is illustrated a method of an adjustable detection threshold scheme in accordance with various embodiments. The method illustrated in FIG. 4 involves implementing 402 a cardiac activity detection and recording scheme to achieve a predetermined objective based on patient and/or device factors (or physician objectives). The method of FIG. 4 involves sensing 404 cardiac signals from a patient and detecting cardiac events based on a multiplicity of detection thresholds and an occurrence threshold for each detection threshold. The method also involves limiting 406 recording of cardiac signal data only to selected cardiac events in order to achieve the predetermined objective. The method of FIG. 4 may optionally involve counting 408 each occurrence of a cardiac signal that meets or exceeds each of the detection thresholds.

The cardiac activity detection and recording scheme illustrated in FIG. 4 can be implemented to provide for a greater or lesser number of cardiac signal data recordings (e.g., ECG strips) depending on the status of a given patient. For example, a physician may specify that a greater number of ECG strips be recorded for an elderly patient with a compromised cardiovascular system (e.g., congestive heart failure), and a lesser number of ECG strips for a young patient with mild atrial fibrillation. The cardiac activity detection and recording scheme illustrated in FIG. 4 can be modified to achieve the desired volume of ECG strip recordings that is appropriate for a particular patient. By way of further example, the patient monitoring device may have a specified battery life and/or memory capacity (or other design constraint). The cardiac activity detection and recording scheme can be modified to ensure that an adequate volume of ECG strip recordings are captured for a particular patient in view of the limited battery life and/or memory capacity of the device.

Modifying the cardiac activity detection and recording scheme may involve a number of parameters, including the value of an initial detection threshold and additional detection thresholds that are subsequently generated, the number of cardiac events at each detection threshold that triggers an ECG strip recording, the spacing between adjacent detection thresholds (e.g., detection zones), among other parameters, and the time period during which cardiac activity is compared against a detection threshold(s). In some embodiments, these and other parameters can be preset by the physician and modified as desired during patient monitoring. In other embodiments, the device may be configured to establish and modify (e.g., self-learn) at least some of these parameters. In further embodiments, both the physician and the device are involved in establishing and modifying the parameters of a cardiac activity detection and recording scheme in accordance with the present disclosure.

Figure 5:
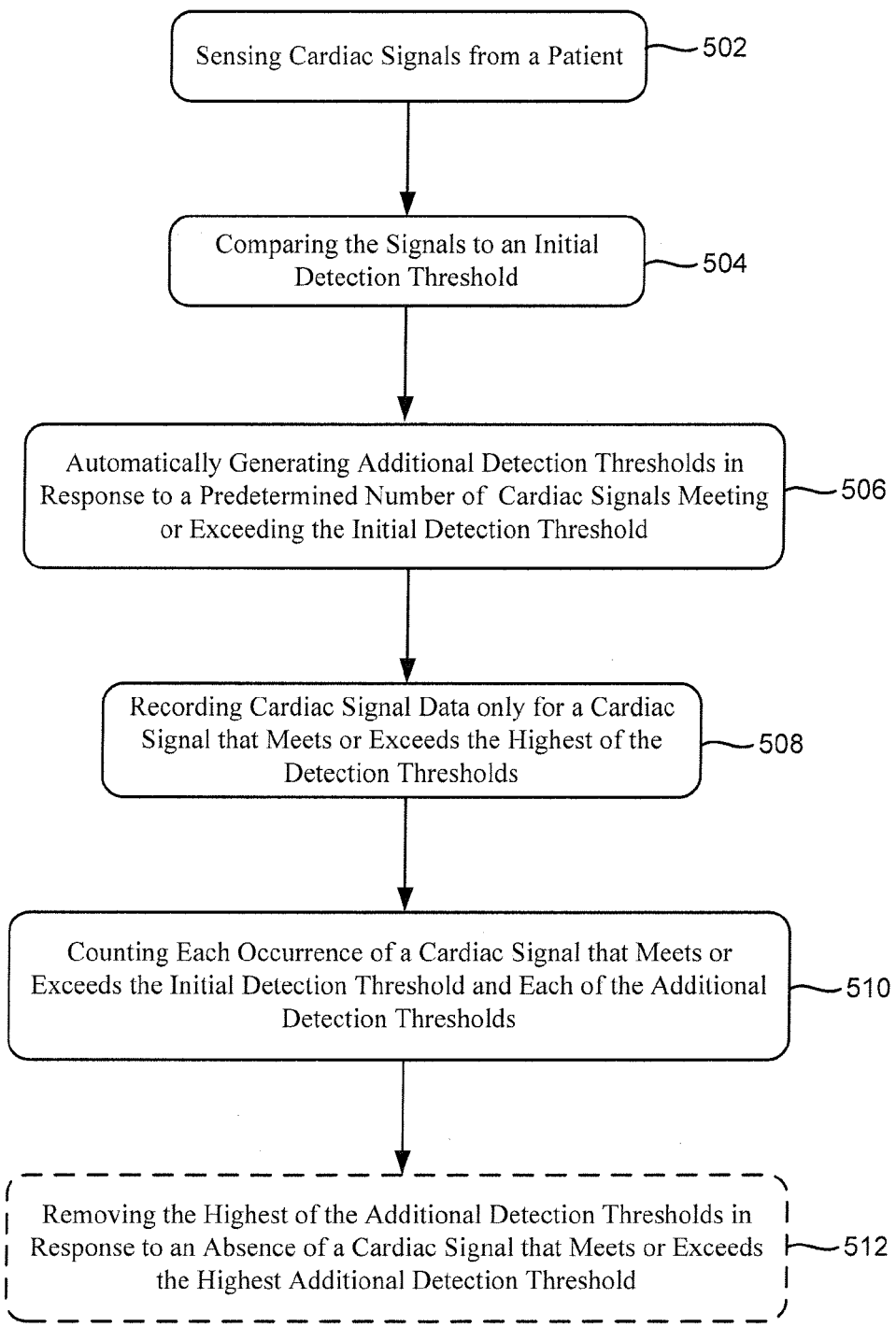
FIG. 5 illustrates an adjustable detection threshold methodology that can be implemented by a patient monitoring device in accordance with further embodiments.

The methodology shown in FIG. 5 and other figures can be implemented by a patient monitoring device according to various embodiments. The method shown in FIG. 5 involves sensing 502 cardiac signals from a patient, and comparing 504 the signals to an initial detection threshold. The initial detection threshold can be a threshold preset by a physician or preset within the device. The method shown in FIG. 5 further involves automatically generating 506 additional detection thresholds in response to a predetermined number of cardiac signals meeting or exceeding the initial detection threshold.

The method shown in FIG. 5 also involves recording 508 cardiac signal data only for a cardiac signal that meets or exceeds the highest of the detection thresholds. The method further involves counting 510 each occurrence of a cardiac signal that meets or exceeds the initial detection threshold and each of the additional detection thresholds. The method shown in FIG. 5 may optionally involve removing 512 the highest of the additional detection thresholds in response to an absence of a cardiac signal that meets or exceeds the highest additional detection threshold over a preset time or adaptive time period (e.g., over 1, 2, or 3 days) or over an adaptive time period (e.g., based on disease condition, patient condition, reaching a boundary condition, etc.).

The methodology illustrated in FIG. 5 ensures that all tachycardia events (or other cardiac events of interest to be monitored) meeting or exceeding a physician-set threshold and automatically adjusted thresholds are counted, but that cardiac signal data (e.g., ECG strip) is recorded for some, but not all, of the detected tachycardia events. A reduction in the number of ECG signal recordings (e.g., less than the number of detected cardiac events) provides for a concomitant reduction in memory, battery usage, and overall data burden. Such a reduction in ECG signal recordings eliminates redundant data (e.g., similar ECG data captured within the same tachycardia detection zone), while providing sufficiently detailed information on representative cardiac events occurring at each of the different threshold levels (e.g., each of the tachycardia detection zones, such as 100-110 bpm, 110-120 bpm, 120-130 bpm, 130-140 bpm. etc. for a delta set to 10 bpm).

Figure 6:
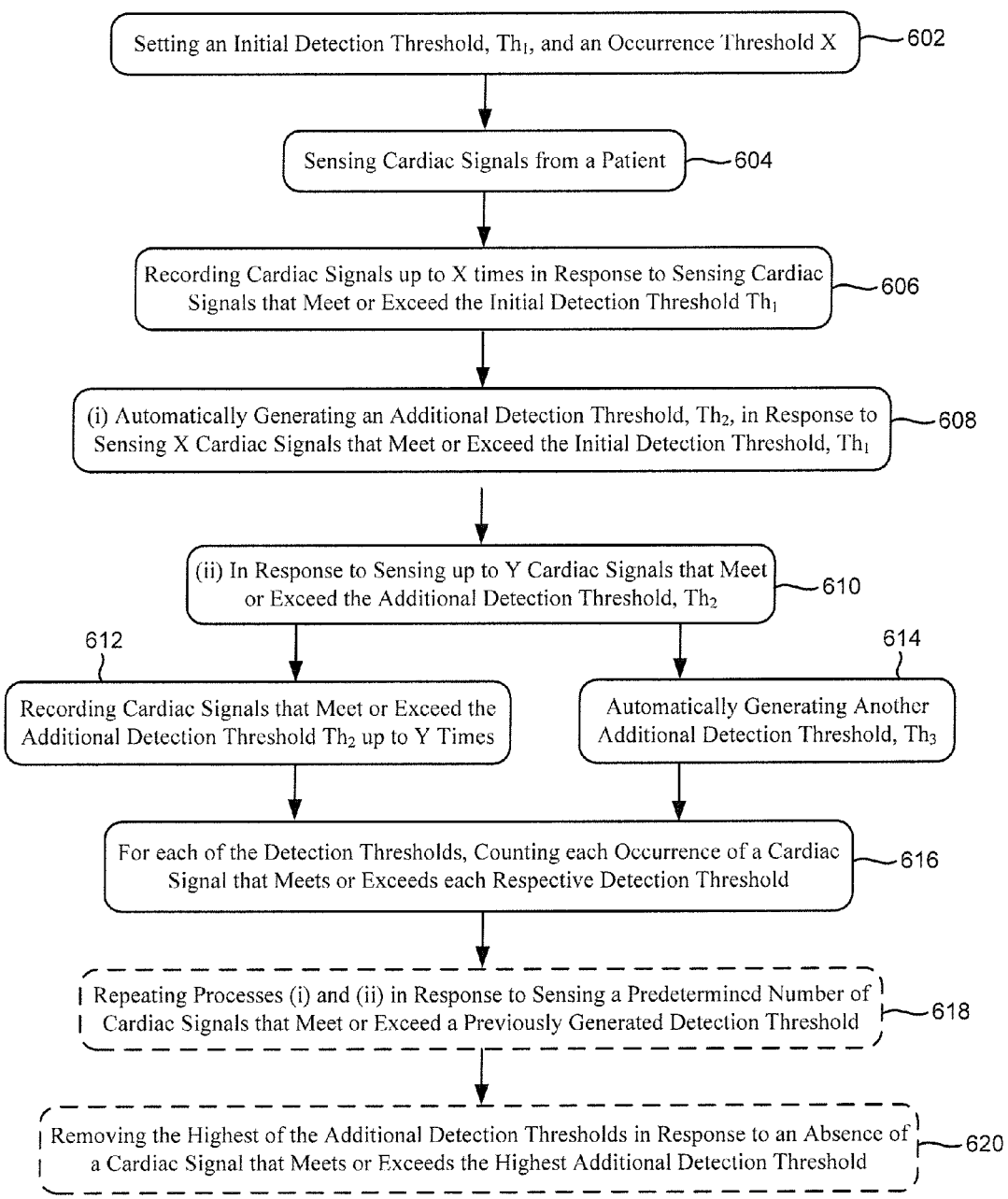
FIG. 6 illustrates an adjustable detection threshold methodology that can be implemented by a patient monitoring device in accordance with various embodiments.

FIG. 6 illustrates a method of an adjustable detection threshold scheme in accordance with further embodiments. The method shown in FIG. 6 involves setting 602 and initial detection threshold, $Th_1$, and an occurrence threshold X, where X is a positive integer. The method involves sensing 604 cardiac signals from a patient, and recording 606 cardiac signals up to X times in response to sensing cardiac signals that meet or exceed the initial detection threshold, $Th_1$. The method shown in FIG. 6 also involves (i) automatically generating 608 an additional detection threshold, $Th_2$, in response to sensing X cardiac signals that meet or exceed the initial detection threshold, $Th_1$. In response (ii) to sensing 610 up to Y cardiac signals that meet or exceed the additional detection threshold, $Th_2$, the method of FIG. 6 involves recording 612 cardiac signals that meet or exceed the additional detection threshold, $Th_2$, up to Y times, and automatically generating 614 another additional detection threshold, $Th_3$.

For each of the detection thresholds, $Th_1$, $Th_2$, and $Th_3$, the method involves counting 616 each occurrence of a cardiac signal that meets or exceeds each respective detection threshold, $Th_1$, $Th_2$, and $Th_3$. The method shown in FIG. 6 may optionally involve repeating 618 processes (i) of block 608 and (ii) of block 610 in response to sensing a predetermined number of cardiac signals that meet or exceed a previously generated detection threshold. The method of FIG. 6 may also optionally involve removing 620 the highest of the additional detection thresholds in response to an absence of a cardiac signal that meets or exceeds the highest additional detection threshold. It is noted that the method of FIG. 6 shows the generation of three detection thresholds for purposes of simplicity, and that more than three (e.g., 4-15) detection thresholds can be generated based on patient and/or device factors. In some embodiments, the occurrence thresholds (e.g., X and Y) can be the same value or be different values. The step size between adjacent detection thresholds, referred to herein as a Delta increment, can be fixed or variable.

Figure 7:
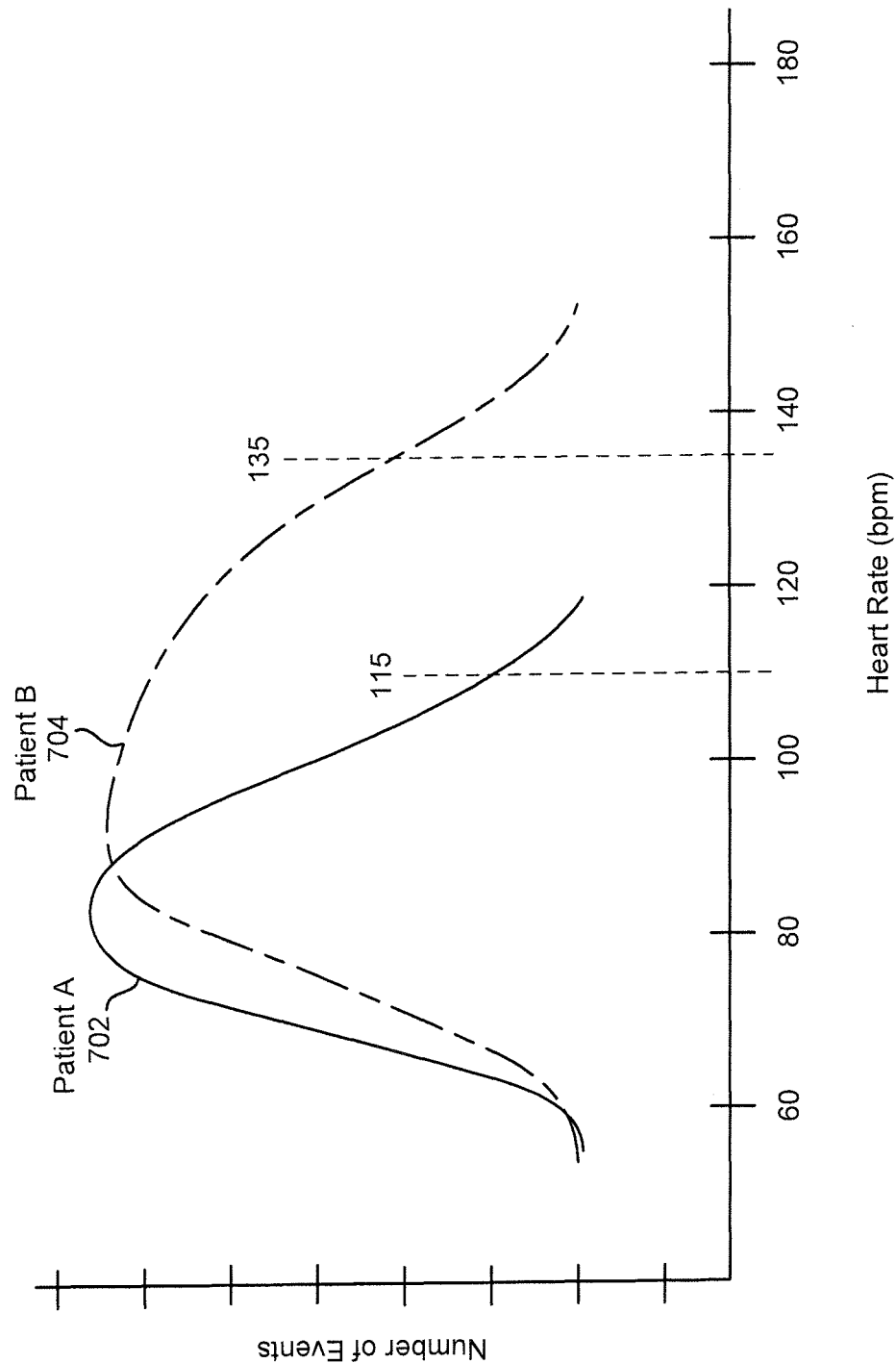
FIG. 7 illustrates histograms developed for two representative patients over a period of time for purposes of determining appropriate detection thresholds in accordance with various embodiments.

Turning now to FIG. 7, there is illustrated a pair of histograms 702 and 704 developed for two patients, Patient A and Patient B. According to various embodiments, a histogram of patient heart rate can be developed over a period of time for purposes of determining appropriate detection thresholds for detecting one or more cardiac events experienced by the patient. A patient histogram can be developed for purposes of establishing an initial detection threshold, rather than the initial detection threshold being set by a physician. A patient histogram may also be developed for purposes of tailoring an initial detection threshold and automatically generated detection thresholds to a specific patient by a patient monitoring device operating in a closed-loop manner.

According to some embodiments, the patient histograms 702 and 704 shown in FIG. 7 represent tallies of different cardiac rhythms detected over a sufficiently long period of time or a specific time period (e.g. night vs day histograms) in order to determine what is normal for the individual patient. The distributions of cardiac rhythms shown in the histograms 702 and 704 are specific to each patient. The histogram 702 indicates that Patient A has a heart rate that falls within a relatively narrow range (e.g., about 60 BPM to about 120 bpm). The histogram 704 indicates that Patient B has a heart rate that falls within a relatively broad range (e.g., about 60 bpm to about 150 bpm). The patient monitoring device or PDM (or a remote server) can be configured to calculate an initial detection threshold based on a patient histogram in accordance with various embodiments. In general terms, the histogram is evaluated to determine a heart rate which is beyond the typical range of the patient based on data contained within the histogram. Such a heart rate analysis can serve as an input to the initial detection threshold (e.g., an initial or subsequently generated detection threshold).

Various mathematical techniques can be used to calculate the initial detection threshold, such as a standard deviation (e.g., 1, 2, or 3 sigma), for example. In the case of histogram 702 for Patient A, for example, the initial detection threshold is calculated as 115 bpm. In the case of histogram 704 for Patient B, for example, the initial detection threshold is calculated as 135 bpm. Although the use of histograms is particularly useful for establishing the initial detection threshold, histograms can be used to refine the initial detection threshold and subsequently generated additional detection thresholds as more patient cardiac activity data is accumulated and analyzed over time. Embodiments that employ a histogram of cardiac activity provide for an adjustable detection threshold scheme that can self-learn an initial detection threshold in accordance with various embodiments. Such analysis can be used for tachycardia rhythm thresholds as illustrated in FIG. 7, for bradycardia rhythm thresholds using the lower tail of the histogram, and/or for other arrhythmias such as atrial fibrillation using R-R variability histograms, among others.

A patient histogram, such as those shown in FIG. 7, can be used to detect patterns of patient heart activity on a daily, weekly or monthly basis. A histogram, by its nature, effectively removes the time element of the information it contains. Developing a histogram over a 24 hour period of time allows for correlation of the histogram data to a patient's diurnal cycle, for example. By evaluating a multiplicity of 24 hour histograms, the device can distinguish between day and night cardiac activity patterns, for example, and adapt its threshold detection scheme accordingly. For example, a relatively high heart rate may be appropriate for a period during daytime, such as during patient exercise, whereas a high heart rate while sleeping would be considered abnormal and potentially indicate presence of a tachyarrhythmia. A similar example could be for bradycardia, where a daytime low threshold for heart rate could indicate an arrhythmia while a nighttime low threshold for heart rate could be normal for a given patient.

Figure 8:
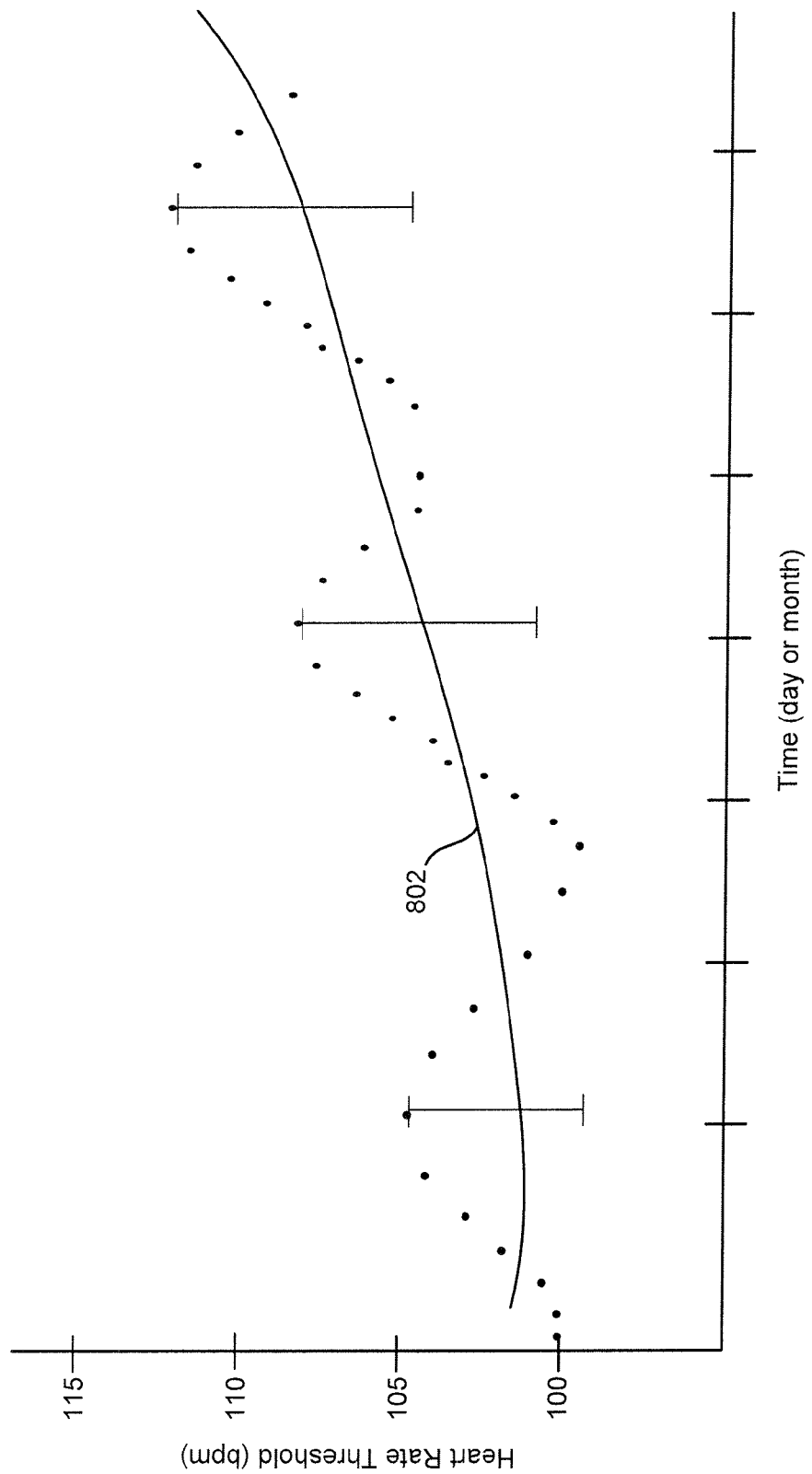
FIG. 8 illustrates a series of short term thresholds developed for a patient for purposes of detecting patterns in patient activity or condition which can result in adjustment of a detection threshold scheme implemented by a patient monitoring device in accordance with various embodiments.

With reference to FIG. 8, the device can learn more sophisticated patient patterns from threshold and occurrence data acquired over the course of a week or a month (or any desired period of time, such as a year or more), for example. A particular patient, for example may routinely exercise on the same three days of the week. The device can learn this routine exercise pattern based on threshold and occurrence data acquired over a multiplicity of weeks. When a familiar pattern is detected by the device, the detection threshold scheme can be adjusted accordingly. For example, upon detecting an exercise pattern using cardiac activity threshold and occurrence data for a particular patient, the Delta increment can be increased so that a higher heart rate is required to cause automatic generation of additional detection thresholds and, therefore, possible ECG strip recordings. Increasing the Delta increment in response to detecting a patient's exercise pattern from threshold and occurrence data reduces the number of superfluous ECG strips that would otherwise be recorded.

FIG. 8 shows a pattern of heart rate detection thresholds (indicated by dots) that track the cardiac activity level of a patient over multiple days or months. The curve 802 represents trending of the detection thresholds over time. The device can be programmed to detect the cyclic or repetitive patterns of the detection thresholds and make appropriate adjustments to the detection threshold scheme to meet desired design objectives, such as limiting the number of ECG strips to avoid redundancy, meeting a specified battery service life goal or operating within a specified device memory capacity constraint, for example. Various mathematical operations can be performed on the data shown in FIG. 8 to determine patterns or other relationships in the detection threshold data, such operations including one or more of a correlation operation (e.g., feature correlation coefficient computation), a standard deviation operation, regression analysis, dependence analysis, distribution analysis, and any other useful mathematical comparison operation or combination of operations. Various trending algorithms (e.g., any of those listed above) can be implemented to detect chronic (long term, e.g., over several days, months or years) changes in the detection thresholds that can indicate stability or progression of a disease. Comparisons can be made between the detection thresholds for a multiplicity of day periods to detect acute changes (short term changes) in patient condition. For example, patient compliance to a medicine regime (e.g., beta blockers or anti-arrhythmic drugs) can be analyzed by comparing changes in detection thresholds on a day-to-day basis. Statistically relevant changes in day-to-day detection thresholds can be detected and reported to the physician.

According to other embodiments, the patient monitoring device or PDM can be configured to read markers on an ECG (or an EGM or electrogram) to determine the range of heart rate variability within a given time frame. For example, if the device sees heart rate variability within a given time period of more than 10 bpm, then fluctuations of more than 10 bpm can be considered within the typical range for that particular patient. As such, the device establishes a detection threshold increment that is above this typical fluctuation range.

Figure 9:
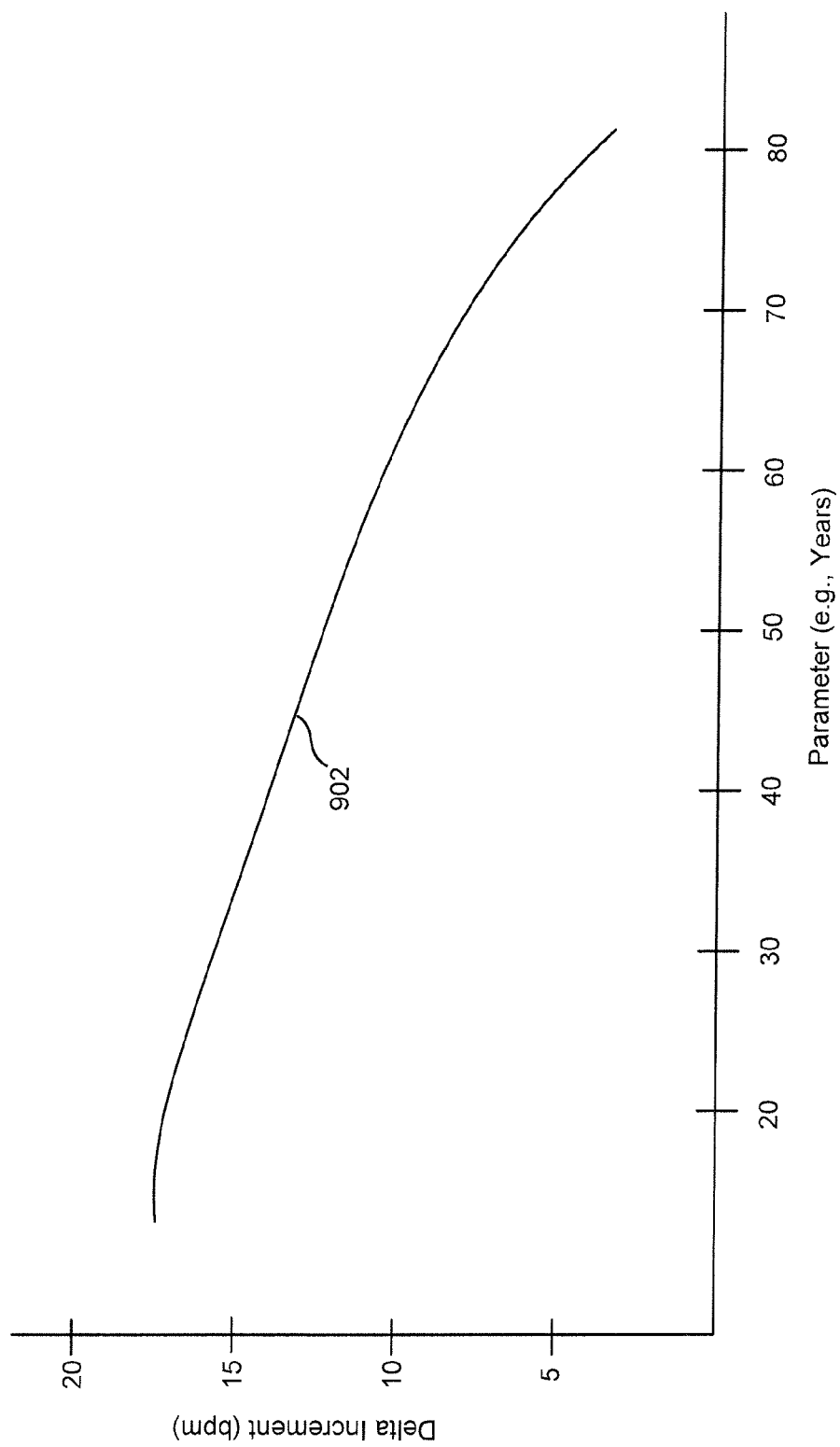
FIG. 9 is a graph that shows a representative relationship between detection threshold increments, referred to as Delta increments (in bpm), and a specified parameter according to an illustrative embodiment.

FIG. 9 shows a graph of Delta increments (in bpm) as a function of a specified parameter according to an illustrative embodiment. The parameter may be any parameter of interest, such as patient age, disease type, physician setting, severity of detected threshold crossing (arrhythmia), etc. For purposes of illustration, and not of limitation, the relationship between the Delta increment and parameter shown in FIG. 9 will be described in the context of patient age. The Delta curve 902 shown in FIG. 9 illustrates a relationship between a device's Delta increment used by an adjustable detection threshold algorithm in relation to a patient's age. The Delta curve 902 shows that younger patients have a correspondingly higher Delta increment due to a relatively broad heart rate range, while older patients have a correspondingly lower Delta increment due to a relatively narrow heart rate range. Use of a Delta curve 902 such as that shown in FIG. 9 by the patient monitoring device allows for tailoring the resolution of Delta increments (e.g., the size of the increments) to the patient's age. According to various embodiments, the Delta curve 902 can be developed from population data, and can be adjusted based on the specific cardiovascular status of a given patient. A similar relationship can be derived between delta increments and disease type, physician selection, severity of detected threshold crossing, among other parameters.

Figure 10:
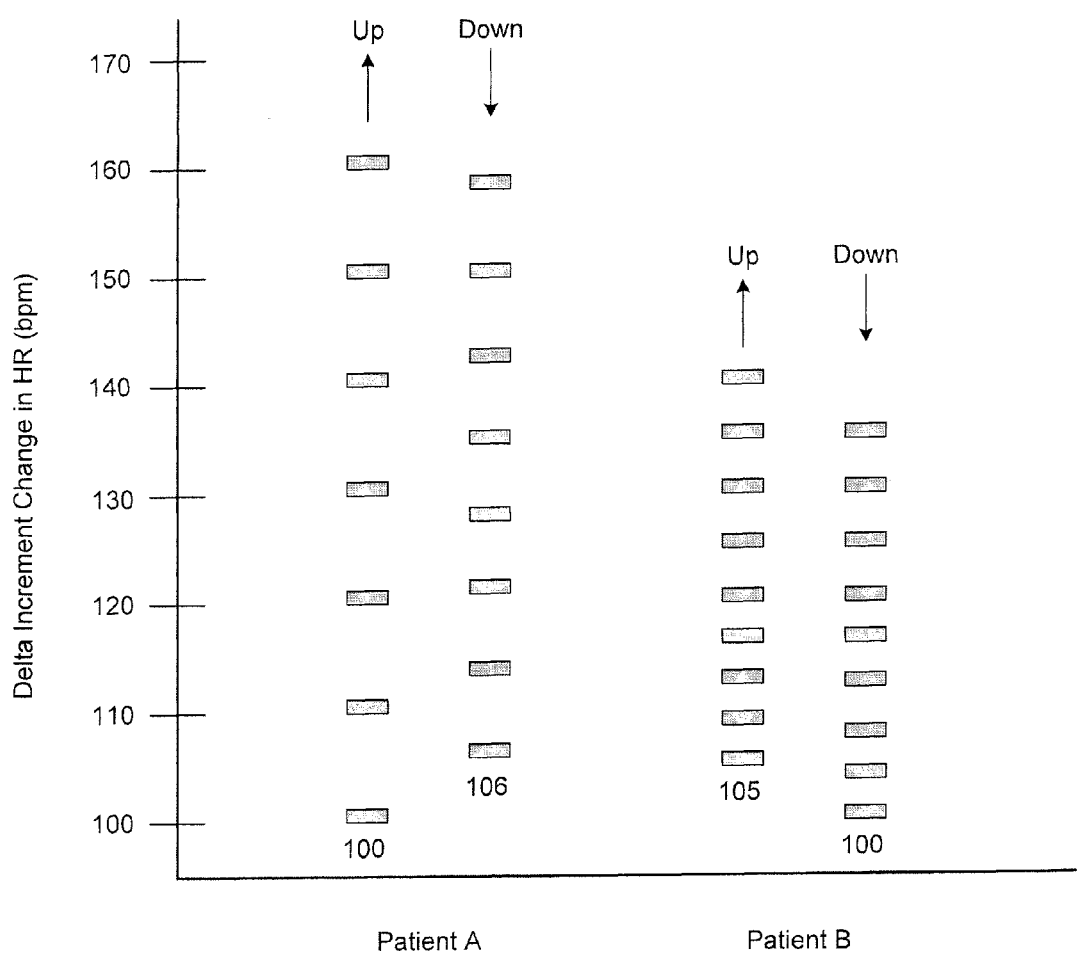
FIG. 10 illustrates a graph of Delta increment change in heart rate (bpm) for two patients according to various embodiments.

FIG. 10 illustrates a graph of Delta increment change in heart rate (bpm) for two patients, Patient A and Patient B, according to various embodiments. In some embodiments, an adjustable detection threshold scheme can employ a fixed or variable Delta increment. As can be seen in FIG. 10, and with respect to Patient A, an initial detection threshold is set by the physician or by the device at 100 bpm. In response to increasing patient heart rate (indicated by the up arrow), additional detection thresholds are generated at a fixed Delta increment of 10 bpm. In response to decreasing patient heart rate (indicated by the down arrow), reduction or removal of detection thresholds results from use of a fixed Delta increment that differs from the increasing fixed Delta increment in terms of size.

The decreasing Delta increment can be larger or smaller than the increasing Delta increment. In FIG. 10, the decreasing Delta increment is illustrated as being smaller than the increasing Delta increment. FIG. 10 also shows that the lowest detection threshold (i.e., ending detection threshold) for the decreasing Delta increment scenario, which was previously the initial detection threshold of 100 bpm, has now been changed to 106 bpm. In this illustrative example, the device has 'learned' that 106 bpm, rather than 100 bpm, is a more appropriate initial detection threshold for purposes of increasing the efficiency of ECG strip capture for Patient A. It can be appreciated that continuing the adjustable detection threshold scheme depicted in FIG. 10 for Patient A over an appreciable duration of time will result in the initial (i.e., lowest) detection threshold tracking the cardiac state of Patient A. As such, the initial or lowest detection threshold can serve as both a cardiac event threshold for detecting a certain cardiac event and a diagnostic metric for monitoring the cardiac condition of the patient over time.

FIG. 10 further shows increasing and decreasing detection thresholds for Patient B, whose heart rate fluctuates within a relatively narrow range. Because of this narrow heart rate range, the Delta increment between detection thresholds is relatively small in comparison to that of Patient A. As in the case of Patient A, the initial detection threshold of 105 bpm differs from that of the ending detection threshold, which in this illustrative embodiment is lower than the initial detection threshold (i.e., 100 bpm).

In some embodiments, the resolution adjustments between Delta increment changes can be learned by the device, such as by the use of histograms. In other embodiments, the device can calculate a recommended Delta increment or detection threshold, communicate this recommendation to the PDM or other patient-external device, which can then be considered by the physician. In response, the physician may indicate acceptance of the device recommended change or input his or her desired change to the Delta increment or detection threshold value. According to some embodiments, the patient monitoring device can be programmed to generate a message in response to meeting or exceeding an initial detection threshold or any additional detection thresholds. The message can be transmitted from the patient recording device to the PDM, which may then communicate the message to a physician's local device via the cloud, the Internet, or other communication network.

In accordance with some embodiments, the detection threshold scheme implemented by an implantable patient monitoring device can be adjusted to achieve a specified device performance requirement. For example, a particular patient monitoring device may have a specified battery life of Z years (e.g., 2-5 years), and the adjustable detection threshold scheme can be configured to provide a satisfactory level of patient monitoring over the specified duration or prolong the effective life of the device. By way of further example, a particular patient monitoring device may have a finite memory capacity for storing ECG strips, cardiac event counts, and other related data. The adjustable detection threshold scheme can be configured to provide a satisfactory level of patient monitoring given the specific memory resources of the device.

Figure 11:
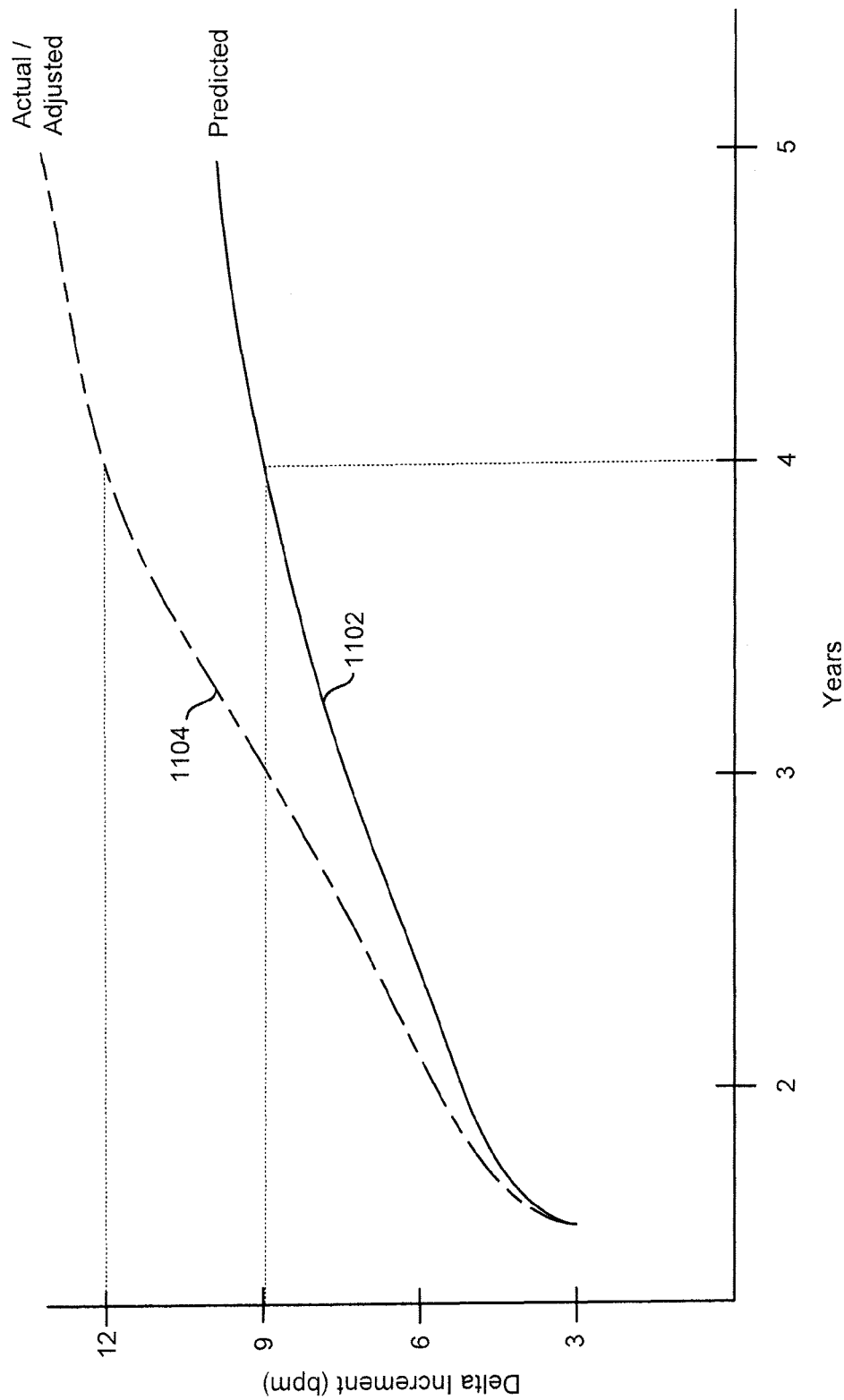
FIG. 11 is a graph showing Delta increments (bpm) as a function of service years for a particular patient monitoring device due to limited battery capacity in accordance with various embodiments.

FIG. 11 is a graph showing Delta increments (bpm) as a function of service years for a particular patient monitoring device due to limited battery capacity in accordance with various embodiments. FIG. 11 generally shows that, for devices having a shorter expected service life (e.g., 2 years), the Delta increment can be set relatively low, such as about 4 or 5 bpm for this device. A relatively low Delta increment allows for the capture of a greater number of ECG strips due to the reduced spacing between adjacent detection thresholds. For devices having a longer expected service life (e.g., 5 years), the Delta increment should be set relatively high, such as about 10 bpm for this device. A relatively high Delta increment allows for the capture of a fewer number of ECG strips due to the increased spacing between adjacent detection thresholds.

Curve 1102 shows the relationship between Delta increments and the number of service years due to limited battery capacity as predicted for the device. The predicted data from which curve 1102 is typically calculated by the device manufacturer. If the design specification requires the device to operate for a minimum of four years, for example, the Delta increment should be set at a value no lower than about 9 bpm. During operation, the device can monitor its battery capacity and compare it to the predicted capacity at a given point in its service life. In FIG. 11, curve 1104 shows the relationship between Delta increments and the number of service years due to limited battery capacity during actual operation. The actual curve 1104 can be compared to the predicted curve 1102 at any point during the service life of the device to adjust the Delta increment parameter.

It can be seen in FIG. 11 that the actual battery capacity at year four for the device is lower than predicted, as indicated by an increase in the Delta increment (which was needed to reduce the number of ECG strip recordings and threshold computations, and therefore battery usage). Accordingly, the device can increase the Delta increment minimum from its original predicted value to a higher value (or lower value) so that the expected battery life requirement can be achieved. In this illustrative example, at year four, the device has increased its Delta increment minimum from about 9 bpm to about 12 bpm. It can be appreciated that adjustment of the Delta increment during the service life of the patient monitoring device can be based on memory capacity limitations or other technical limitation of the device. It can be further appreciated that multiple technical constraints (e.g., battery life and memory capacity) of the device can be used to adjust the section threshold scheme of a patient monitoring system. In another embodiment, the relationship described in FIG. 11 can be based on the count X of the captured data strips and the years of service/battery longevity/memory capacity, such that the number of captured data strips needed before adjusting the threshold can be derived based on the desired performance characteristics of the implantable medical device.

In some embodiments, the patient monitoring device can be programmed to collect physiologic information from a patient on a discontinuous basis. The duration and time separation between adjacent sensing windows can be based on pre-programmed values, on patient-specific factors, and/or adjusted dynamically. For example, physiologic information can be collected several times per day, such as once every minute, every several minutes, every hour, or every several hours according to a pre-programmed schedule. Physiologic information can be collected every several days and/or in response to detecting predetermined events. These discontinuous (non-overlapping) time-separated sensing windows can have the same or different duration (e.g., difference lengths depending on time of day, activity level, cardiac condition, etc.). The operations discussed herein can include comparisons performed on the ECG signal and/or detection thresholds captured in/computed for a multiplicity of time-separated sensing windows. For example, detection of a potentially concerning cardiac condition can trigger opening of one or more addition (i.e., out-of-sequence) sensing windows in order to further assess the potentially concerning cardiac condition. The patient monitoring device can evaluate cardiac and non-cardiac signal information (optionally) acquired for each of these sensing windows to provide a more accurate assessment of the potentially concerning cardiac condition of the patient.

Figure 12:
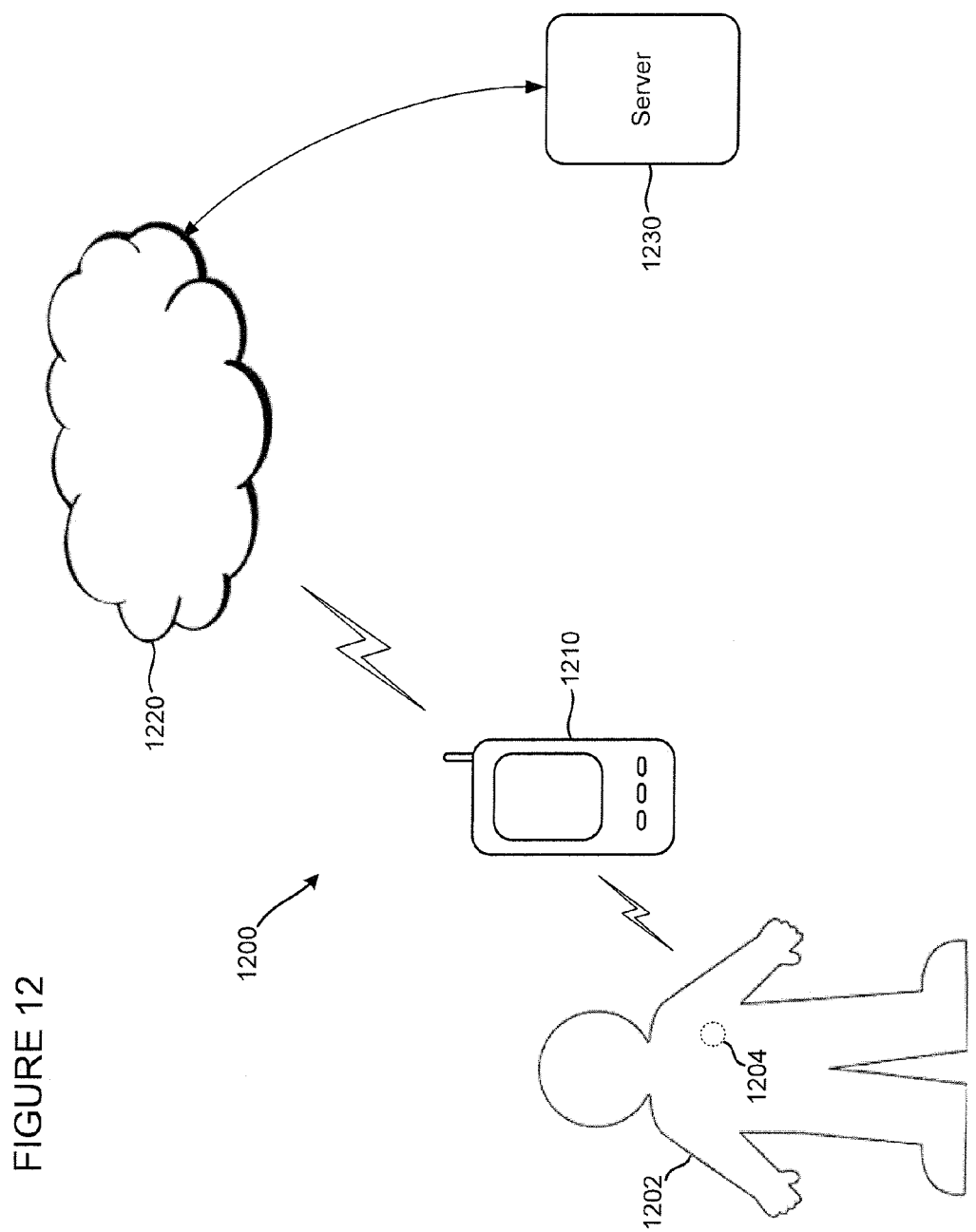
FIG. 12 is a diagram of a representative system for assessing a patient using an adjustable detection threshold methodology in accordance with various embodiments.

A patient monitoring device of a type disclosed herein can be embodied in an implantable device (e.g., subcutaneous extra-thoracic device, intra-thoracic device), a cutaneous patient-external device, or a hybrid device having both patient-internal and patient-external components. A patient monitoring device of a type disclosed herein can be incorporated in a variety of system implementations, a representative example of which is shown in FIG. 12. The system 1200 includes a patient monitoring device 1204 implanted in a body of a patient 1202. The device 1204 may correspond to any of the patient monitoring devices disclosed herein. When implanted, the device 1204 may collect physiological data from the patient 1202. A handheld computing device 1210, such as a PDM, may be programmed to communicate wirelessly (e.g., transmit or receive data via radio frequency telemetry) with the implantable device 1204. In some implementations, an external charging device (not shown) may be used to periodically recharge a battery of the implantable device 1204, though the device 1204 may alternatively use a single-use battery in some implementations.

In various implementations, the patient 1202 may use the handheld device 1210 to manually initiate data collection by the device 1204 (e.g., initiate ECG signal sensing and recording). For example, if the patient 1202 feels lightheaded or feels palpitations in her chest, she may press a button on the handheld device 1210, and the handheld device 1210 may wirelessly command the device 1204 to record and store physiologic data. The device 1204 may also record a physiologic signal when it determines that such recordation may provide useful information. For example, the device 1204 may monitor a physiologic parameter (e.g., heart rate), and may record an ECG signal based on predetermined characteristics of the physiologic parameter. According to various implementations, the device 1204 can be configured to record sensed physiologic information according to a predetermined schedule, in addition to recording at least ECG data and event counts in according with an adjustable detection threshold scheme described hereinabove.

The device 1204 may periodically transmit collected data to the handheld device 1210, such as every few hours or once per day, for example. The device 1204 may also transmit collected data (e.g., ECG strips and event counts) in response to events detected during execution of an adjustable detection threshold scheme described hereinabove. In some implementations, the device 1204 may transmit sensed data in real time to the handheld device 1210, and the handheld device 1210 may store the data in internal memory or display the data as a waveform or otherwise on a display screen of the handheld device 1210. The handheld device 1210 is configured to wirelessly communicate with the cloud 1220 (e.g., the Internet) via a cellular or Wi-Fi connection, and to establish a connection with a remote server 1230. The handheld device 1210 may send and receive data to/from the server 1230. In some embodiments, the handheld device 1210 may transmit data through the cloud 1220 and to the remote server 1230, where the data may be processed and analyzed automatically (e.g., algorithmically by the server 1230) and/or by a physician or a health care provider. Thresholds can be computed and/or verified at the server 1230 and transmitted to handheld device 1210 for upload to the device 1204. In some implementations, data analysis may occur within one or both of the device 1204 and the handheld device 1210 (or in a distributed manner between two or more of these components). Data analysis can include detection of cardiac events/disease progression and other anomalies based on the collected data and trending of such detection and threshold data. Data analysis can also include monitoring and tracking of a disease status of the patient 1202.

Figure 13:
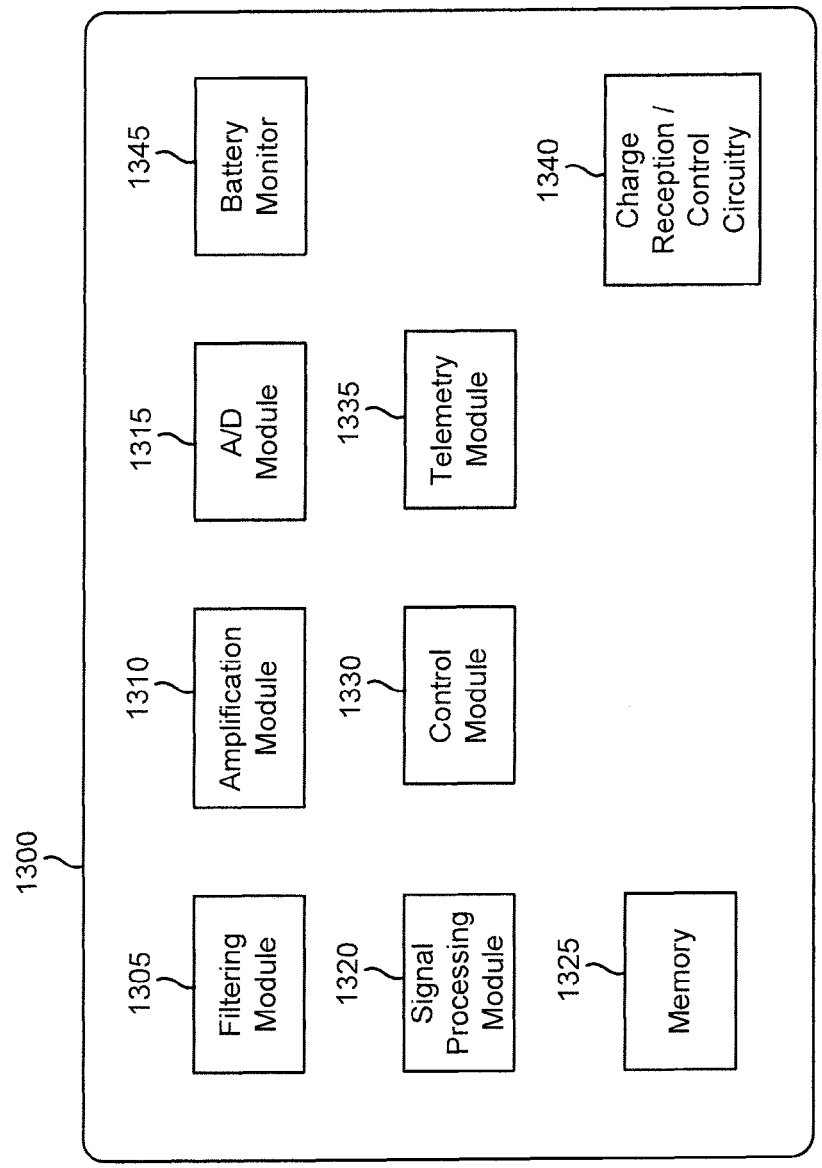
FIG. 13 is a block diagram of circuitry that may be included in implementations of a system for assessing a patient using an adjustable detection threshold methodology in accordance with various embodiments.

FIG. 13 is a block diagram of circuitry 1300 that may be included in implementations of a patient monitoring device disclosed herein. In some implementations, the circuitry 1300 or a portion thereof may be included in the electronics circuitry shown in various preceding figures. Components or modules may be combined or separated as desired, and may be positioned in one or more portions of the implanted device. A filtering module 1305 may receive a sensed physiologic signal and appropriately filter the signal to remove unwanted noise or to compare the received signal to information in a desired frequency range, or above or below a desired frequency threshold. An amplification module 1310 may amplify the received signal for processing, and an analog-to-digital converter 1315 may convert the analog signal to a digital signal. The digital signal may be stored directly into memory 1325, or may first be processed by a signal processing module 1320. Signal processing module 1320 may include functions to extract information from the measured signal, or to compress the measured signal to reduce the volume of data to store and transmit. Memory 1325 may include both volatile and non-volatile memory, according to various implementations, and may additionally store instructions that can be executed by a processor or logic device to perform specified actions. For example, a processor or logic device of a patient monitoring device can be configured to execute programmed instructions to implement an automatic detection threshold adjustment methodology according to the various embodiments disclosed herein.

A control module 1330 may provide overall device control, and may include one or more processors that can execute instructions and in response perform actions. A telemetry module 1335 may be used, in conjunction with the telemetry antenna, for communication with an external device. Charge reception/control circuitry 1340 may optionally be used in implementations that include a rechargeable battery to control reception of charge energy over a charge reception apparatus and coordinate recharging of the battery. A battery monitoring module 1345 may provide one or more of controlling the charge current/voltage as appropriate for the type of battery, providing data that can be transmitted to a charger during charging to control and terminate charge time, assess a state of the battery from charge to depletion via voltage, impedance, charge-counting or other means, provide data to communicate to an external device for feedback as to when to charge or if an early charge is required. For simplicity, connections between the various modules are not shown in FIG. 13.

CONCLUSION

The above description is intended to be illustrative, and not restrictive. For example, the above-described examples (or one or more aspects thereof) may be used in combination with each other. Other examples may be used, such as by one of ordinary skill in the art upon reviewing the above description. Also, in the above Detailed Description, various features may be grouped together to streamline the disclosure. This should not be interpreted as intending that an unclaimed disclosed feature is essential. Rather, inventive subject matter may lie in less than all features of a particular disclosed example.

What is claimed is:

1. A method, comprising:
sensing cardiac signals and comparing the signals to an initial detection threshold;
automatically generating an additional detection threshold in response to a predetermined number of the cardiac signals meeting or exceeding: the initial detection threshold or a previously generated detection threshold;
concurrently counting each occurrence of a cardiac signal meeting or exceeding each of the detection thresholds; and
recording cardiac signal data only for a cardiac signal of the sensed cardiac signals that meets or exceeds the highest of the detection thresholds.

2. The method of claim 1, wherein automatically generating the additional detection threshold comprises:
automatically generating a plurality of additional detection thresholds;
recording cardiac signal data only for a cardiac signal of the sensed cardiac signals that meets or exceeds the highest of the detection thresholds; and
counting each occurrence of a cardiac signal that meets or exceeds the initial detection threshold and each of the plurality of additional detection thresholds.

3. The method of claim 1, comprising removing the highest of the additional detection thresholds in response to an absence of a cardiac signal of the sensed cardiac signals that meets or exceeds the highest additional detection threshold over a fixed or adaptive time period.

4. The method of claim 3, comprising repeating removing the highest additional detection threshold until only the initial detection threshold is operative for recording cardiac signals.

5. The method of claim 1, wherein the additional detection threshold is offset from the initial detection threshold or the previously generated detection threshold by a fixed value.

6. The method of claim 1, wherein the additional detection threshold is offset from the initial detection threshold or the previously generated detection threshold by a value that can vary over time.

7. The method of claim 1, wherein the predetermined number of cardiac signals needed to meet or exceed the initial detection threshold or a previously generated detection threshold is a fixed or varying integer.

8. The method of claim 1, wherein the additional detection thresholds are indicators of a cardiac status of the patient.

9. The method of claim 8, comprising trending the additional detection thresholds over time.

10. A method, comprising:
(a) setting an initial detection threshold $Th_1$ and an occurrence threshold X, where X is a positive integer;
(b) sensing cardiac signals from a patient;
(c) recording cardiac signals up to X times in response to sensing cardiac signals that meet or exceed the initial detection threshold $Th_1$;
(d) automatically generating an additional detection threshold $Th_2$ in response to sensing X cardiac signals that meet or exceed the initial detection threshold $Th_1$;
(e) in response to sensing up to Y cardiac signals that meet or exceed the additional detection threshold $Th_2$:
(i) recording cardiac signals that meet or exceed the additional detection threshold $Th_2$ up to Y times; and
(ii) automatically generating another additional detection threshold $Th_3$; and
(f) for each of the respective detection thresholds $Th_1$, $Th_2$, and $Th_3$, counting each occurrence of a cardiac signal that meets or exceeds each respective detection threshold, $Th_1$, $Th_2$, and $Th_3$.

11. The method of claim 10, wherein processes (d) and (e) are repeated in response to sensing a predetermined number of cardiac signals that meet or exceed a previously generated detection threshold.

12. The method of claim 10, comprising removing the highest of the additional detection thresholds in response to an absence of a cardiac signal that meets or exceeds the highest additional detection threshold over a fixed or adaptive time period.

13. The method of claim 10, wherein the additional detection threshold is offset from the initial detection threshold or the previously generated detection threshold by a fixed value or a value that can vary over time.

14. The method of claim 10, comprising trending the additional detection thresholds over time to assess changes in a cardiac status of the patient.

15. The method of claim 10, wherein setting the initial detection threshold or generating an additional detection threshold comprises:
   determining a typical range for the cardiac signals specific to the patient; and
   setting the initial detection threshold or the additional detection threshold to a value that is beyond the typical range.

16. A medical device, comprising:
   a housing configured for implantation within a body of a patient;
   detection circuitry disposed in the housing and coupled to an electrode arrangement, the detection circuitry configured to sense cardiac signals from the patient; and
   a processor coupled to the detection circuitry, the processor configured to compare the cardiac signals to an initial detection threshold, automatically generate an additional detection threshold in response to a predetermined number of the cardiac signals meeting or exceeding: the initial detection threshold or a previously generated detection threshold, concurrently count each occurrence of a cardiac signal meeting or exceeding each of the respective detection thresholds, and record cardiac signal data only for a cardiac signal of the sensed cardiac signals that meets or exceeds the highest of the detection thresholds.

17. The device of claim 16, wherein the processor is configured to automatically generate a plurality of additional detection thresholds, record cardiac signal data only for a cardiac signal of the sensed cardiac signals that meets or exceeds the highest of the detection thresholds, and count each occurrence of a cardiac signal of the sensed cardiac signals that meets or exceeds the initial detection threshold and each of the plurality of additional detection thresholds.

18. The device of claim 16, wherein the processor is configured to remove the highest of the additional detection thresholds in response to an absence of a cardiac signal of the sensed cardiac signals that meets or exceeds the highest additional detection threshold.

19. The device of claim 16, wherein the additional detection thresholds are indicators of a cardiac status of the patient, and the processor is configured to trend the additional detection thresholds over time.

20. The device of claim 16, wherein the processor is configured to determine a typical range for the cardiac signals, and set the initial detection threshold or the additional detection threshold to a value that is beyond the typical range.

* * * * *

UNITED STATES PATENT AND TRADEMARK OFFICE
CERTIFICATE OF CORRECTION

PATENT NO. : 9,314,178 B2  
APPLICATION NO. : 14/209035  
DATED : April 19, 2016  
INVENTOR(S) : Rodolphe Katra et al.

It is certified that error appears in the above-identified patent and that said Letters Patent is hereby corrected as shown below:

On the title page

(73) Assignee: GREATBACH, LTD., Clarence, NY (US) should read --GREATBATCH, LTD., Clarence, NY (US)--

Signed and Sealed this
Fourteenth Day of June, 2016

Michelle K. Lee
*Director of the United States Patent and Trademark Office*